United States Patent
Nadler

(10) Patent No.: US 11,065,397 B2
(45) Date of Patent: Jul. 20, 2021

(54) INHALATION DEVICE, INHALATION DEVICE SET, AND NOZZLE PLATE THEREFOR

(71) Applicant: APTAR RADOLFZELL GMBH, Radolfzell (DE)

(72) Inventor: Günter Nadler, Moos-Iznang (DE)

(73) Assignee: Aptar Radolfzell GMBH, Radolfzell (DE)

( * ) Notice: Subject to any disclaimer, the term of this patent is extended or adjusted under 35 U.S.C. 154(b) by 390 days.

(21) Appl. No.: 15/573,647

(22) PCT Filed: May 11, 2016

(86) PCT No.: PCT/EP2016/060605
§ 371 (c)(1),
(2) Date: Nov. 13, 2017

(87) PCT Pub. No.: WO2016/184761
PCT Pub. Date: Nov. 24, 2016

(65) Prior Publication Data
US 2018/0117267 A1    May 3, 2018

(30) Foreign Application Priority Data
May 20, 2015    (EP) .................................... 15168316

(51) Int. Cl.
*A61M 11/00* (2006.01)
*A61M 15/00* (2006.01)
(Continued)

(52) U.S. Cl.
CPC ......... *A61M 11/003* (2014.02); *A61M 11/006* (2014.02); *A61M 11/02* (2013.01);
(Continued)

(58) Field of Classification Search
CPC ............... A61M 11/006; A61M 11/02; A61M 11/0086; A61M 15/0093; A61M 15/009;
(Continued)

(56) References Cited

U.S. PATENT DOCUMENTS 3,186,407 A    6/1965    Morrison
4,715,387 A *  12/1987   Rose ..................... A61M 15/00
                                                131/270

(Continued)

FOREIGN PATENT DOCUMENTS

DE    89 06 590 U1    10/1989
DE    60105031 T2    8/2005
(Continued)

OTHER PUBLICATIONS

International Search Report (with English translation) and Written Opinion of the International Searching Authority issued in Application No. PCT/EP2016/060605, dated Sep. 20, 2016 (27 pages).

(Continued)

*Primary Examiner* — Margaret M Luarca
(74) *Attorney, Agent, or Firm* — Flynn Thiel, P.C.

(57) ABSTRACT

An inhalation device including a housing, which encloses a liquid reservoir in which the liquid is stored before discharge, and an applicator head with a nebulization chamber and an applicator piece connected thereto, wherein the applicator piece is designed either as a mouthpiece, to be received in the mouth of a patient, or as an inhalation mask, to sealingly cover the mouth, the nose, or the mouth and the nose. The inhalation device furthermore has a discharge channel which connects the liquid reservoir to the applicator head. The inhalation device includes at the end of the discharge channel a nozzle plate with a large number of nozzle openings which serve to generate an inhalation mist (Continued)

and through which the liquid from the liquid reservoir is conveyed into the nebulization chamber.

24 Claims, 9 Drawing Sheets

(51) Int. Cl.
*B05B 1/14* (2006.01)
*B65D 83/30* (2006.01)
*A61M 16/06* (2006.01)
*B65D 83/14* (2006.01)
*B65D 83/20* (2006.01)
*B65D 83/24* (2006.01)
*B65D 83/62* (2006.01)
*A61M 16/20* (2006.01)
*A61M 11/02* (2006.01)
*A61M 16/14* (2006.01)

(52) U.S. Cl.
CPC ...... *A61M 15/009* (2013.01); *A61M 15/0021* (2014.02); *A61M 15/0086* (2013.01); *A61M 15/0093* (2014.02); *A61M 16/0605* (2014.02); *A61M 16/14* (2013.01); *A61M 16/201* (2014.02); *B05B 1/14* (2013.01); *B65D 83/205* (2013.01); *B65D 83/206* (2013.01); *B65D 83/24* (2013.01); *B65D 83/30* (2013.01); *B65D 83/62* (2013.01); *B65D 83/754* (2013.01); *A61M 2205/0205* (2013.01); *A61M 2205/071* (2013.01); *A61M 2205/183* (2013.01); *A61M 2205/3334* (2013.01); *A61M 2205/43* (2013.01); *A61M 2205/583* (2013.01); *A61M 2210/0618* (2013.01); *A61M 2210/0625* (2013.01)

(58) Field of Classification Search
CPC ..... A61M 15/0086; A61D 7/00; B65D 83/20; B65D 83/28; B65D 83/384
See application file for complete search history.

(56) References Cited

U.S. PATENT DOCUMENTS

| 6,338,442 | B1 | 1/2002 | De Laforcade |
| 7,481,382 | B2 | 1/2009 | Christ |
| D696,768 | S | 12/2013 | Karlsson et al. |
| 2002/0017575 | A1 | 2/2002 | Andrews et al. |
| 2003/0178507 | A1* | 9/2003 | Maria Rijn Van .... A61M 15/00 239/337 |
| 2004/0129270 | A1 | 7/2004 | Fishman |
| 2006/0118107 | A1 | 6/2006 | King |
| 2006/0213408 | A1 | 9/2006 | Christ |
| 2007/0175469 | A1 | 8/2007 | Rohrschneider et al. |
| 2008/0006719 | A1* | 1/2008 | Clerget ...................... B05B 1/14 239/337 |
| 2009/0050137 | A1 | 2/2009 | Wissink et al. |
| 2011/0290244 | A1* | 12/2011 | Schennum ............ A61M 15/06 128/200.23 |
| 2012/0103326 | A1* | 5/2012 | Karle ....................... A61D 7/04 128/200.21 |
| 2013/0139814 | A1* | 6/2013 | Mullane ............ A61M 15/0086 128/203.12 |
| 2015/0231130 | A1* | 8/2015 | Wynne ................. A61K 9/0043 514/282 |

FOREIGN PATENT DOCUMENTS

| DE | 60208429 | T2 | 6/2006 |
| DE | 202006021269 | U1 | 7/2014 |
| EP | 1 698 399 | A1 | 9/2006 |
| EP | 1 792 660 | A1 | 6/2007 |
| EP | 2 095 883 | A1 | 9/2009 |
| FR | 2 871 712 | | 12/2005 |
| GB | 1 222 121 | | 2/1971 |
| GB | 2 202 591 | A | 9/1988 |
| JP | 2018114857 | A | 7/2018 |
| RU | 121737 | U1 | 11/2012 |
| WO | 0136018 | A2 | 5/2001 |
| WO | WO 02/18058 | A1 | 3/2002 |
| WO | WO 2006/094796 | A1 | 9/2006 |
| WO | WO 2011/147714 | A1 | 12/2011 |
| WO | WO 2013/064690 | A1 | 5/2013 |
| WO | WO 2014/056769 | A1 | 4/2014 |
| WO | WO 2015/149922 | A2 | 10/2015 |

OTHER PUBLICATIONS

European Patent Office Search Report issued in Application No. EP 15 16 8316, with English translation of category of cited documents, dated Oct. 21, 2015 (9 pages).

Third Party Observation Report issued in Application No. EP 15 16 8316, dated Mar. 15, 2017 (3 pages).

Search Report of Russian Patent Office issued in Russian Application No. 2017140877 dated Sep. 19, 2018 (2 pages).

Office Action of Russian Patent Office issued in Russian Application No. 2017140877 with English translation dated Sep. 20, 2018 (24 pages).

Opposition letter cited in corresponding European Patent No. 3297762, dated Sep. 8, 2020 (20 pages).

* cited by examiner

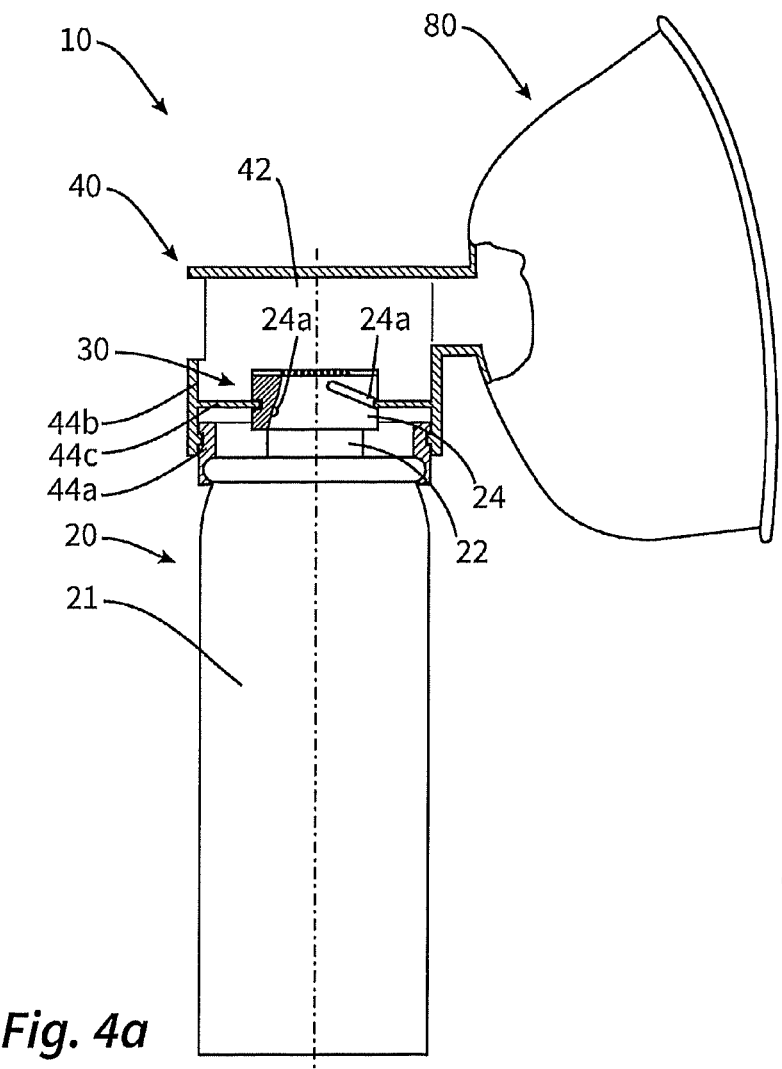
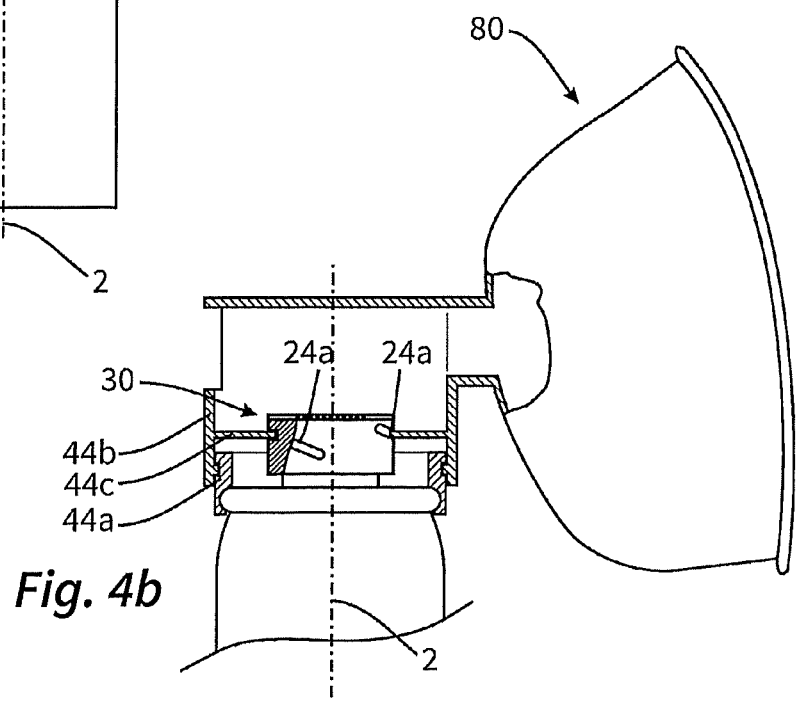
Fig. 4a
Fig. 4b

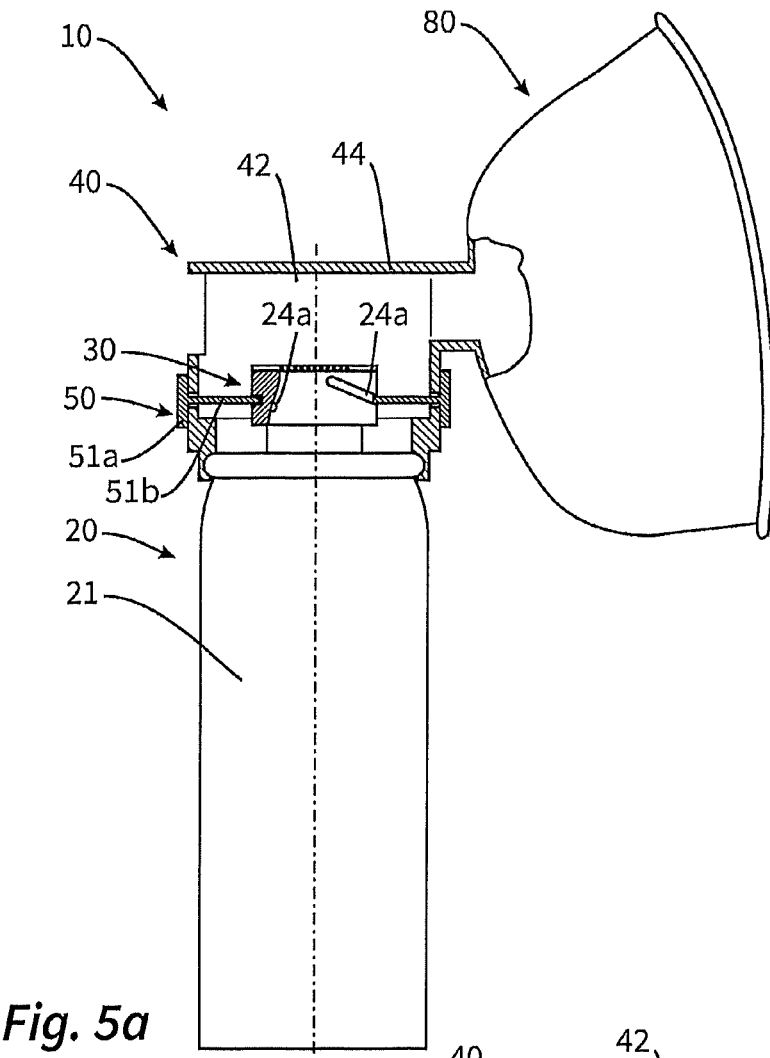
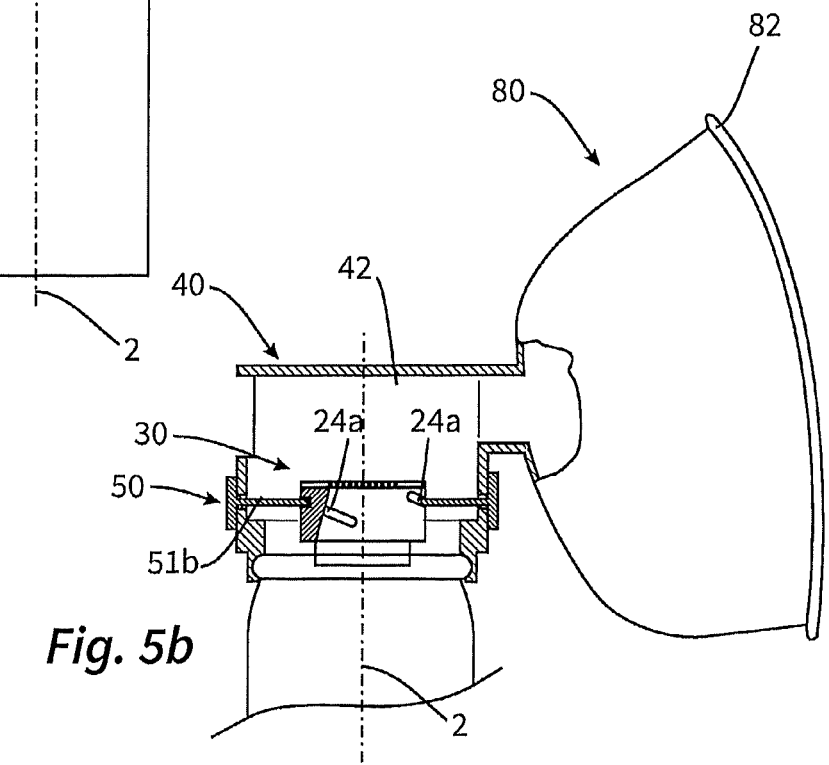
Fig. 5a
Fig. 5b

INHALATION DEVICE, INHALATION DEVICE SET, AND NOZZLE PLATE THEREFOR

FIELD OF USE AND PRIOR ART

The invention relates to an inhalation device for inhaling a liquid in nebulized form. The invention further relates to an inhalation device set.

Inhalation devices for inhaling a liquid in nebulized form are known.

Such inhalation devices have the purpose of nebulizing a liquid such that the latter can be breathed into the airways, the bronchi and the lungs of a patient. In addition to classical medicaments, such inhalation devices are also used in particular for the discharge of saline or of water otherwise supplemented with essential oils. This affords a simple way of allowing cold and flu sufferers to breathe easily again and to relieve pain in the nose, throat and pharynx and also in the lungs by simple means.

Known inhalation devices are usually either of very simple construction, providing not much more than a breathing mask connected to a storage unit, the storage unit having to be refilled for each application, or they are of rather complex construction and in part provided with a power supply in order to permit the nebulization of the liquid. The last-mentioned devices are often not easily transportable.

PROBLEM AND SOLUTION

The problem addressed by the invention is to make available an inhalation device which, compared with the known inhalation devices, is advantageous in terms of transportability, simple structure, easy operation and/or low production costs.

The problem is solved by an inhalation device for inhaling a liquid in nebulized form, the device having a nozzle plate at the end of a discharge channel with a large number of nozzle openings which generate an inhalation mist, or the device having an outlet valve switchable by a rotational movement of the housing.

The inhalation device has a housing, which encloses a liquid reservoir in which the liquid is stored before discharge. The inhalation device has an applicator head with a nebulization chamber and an applicator piece connected thereto, wherein the applicator piece is designed either as a mouthpiece, to be received in the mouth of a patient, or as an inhalation mask, to sealingly cover the mouth, the nose, or the mouth and the nose, or as an adapter piece for fitting a mouthpiece or an inhalation mask. The inhalation device has a discharge channel which connects the liquid reservoir to the applicator head.

According to the invention, the inhalation device is used
  for a liquid with which the liquid reservoir is filled and
    which is one of the following liquids:
  a saline aqueous solution, or
  an aqueous solution in the form of a Ringer's solution or
    a buffered solution, or
  an aqueous solution with at least one of the additives
    carbohydrates, essential oils, menthol and plant
    extracts, or
  an aqueous solution containing vitamins, trace elements,
    manganese or zinc, or
  an aqueous solution with at least one of the additives from
    the group comprising cinnamon oil, tea tree oil, sage
    oil, thyme oil, lemon balm oil.

The inhalation device has, at the end of the discharge channel, the nozzle plate with a large number of the nozzle openings which serve to generate the inhalation mist and through which the liquid from the liquid reservoir is conveyed into the nebulization chamber.

As regards to said liquids, it has been shown that the discharge by means of a nozzle plate is particularly advantageous for the purpose of nebulization. The resulting liquid mist passes particularly effectively into the airways and in particular into the lungs of the user and exerts a positive effect there.

An inhalation device according to the invention has an applicator piece with a shape specially adapted for the inhalation purposes.

The applicator piece can be provided as a mouthpiece for purely oral administration of the inhalation mist. As a mouthpiece, the applicator piece usually has an outlet whose width is greater than its height and which, on the top and bottom, has bearing surfaces on which the upper lip and lower lip bear. By virtue of the bearing surfaces lying opposite each other, the mouthpiece can be securely gripped by the user's lips, which can be advantageous in the case of the valve configurations described below.

As an inhalation mask, the applicator piece usually has a circumferential sealing edge for resting on the face of a user, the sealing edge being dimensioned such that it can enclose the mouth or the nose or the mouth and the nose. The inhalation mask can be provided with retention means, for example an elastic strap, which allows the mask to be positioned securely in front of the mouth and/or nose without having to be specifically held there.

The applicator piece mounted directly on the applicator head can also be an adapter piece, which can be designed for the coupling of a mouthpiece or of an inhalation mask. The mouthpiece and/or the inhalation mask can then be separate parts that accompany the inhalation device for assembly by the end user. In particular, a plug connection can be provided, in which case a plug portion provided on the mouthpiece or on the inhalation mask is pushed into the applicator piece or pushed onto the latter. The plug portion and the applicator piece then preferably establish a force-fit connection.

It is also possible that the applicator piece itself can already be used as a mouthpiece but still allows a plug portion of an accompanying inhalation mask to be plugged in or plugged on.

An outlet of the applicator piece in the form of an adapter piece or as a mouthpiece preferably has a minimum free cross section of between 50 $mm^2$ and 2000 $mm^2$, preferably between 80 $mm^2$ and 800 $mm^2$, in particular between 500 $mm^2$ and 800 $mm^2$.

In an inhalation device according to the invention, an inhalation mist is generated via said nozzle plate with a large number of small nozzles. Such a nozzle plate has a plurality of nozzle openings, preferably 9 or more nozzle openings, particularly preferably 16 or more nozzle openings or 25 or more nozzle openings. These preferably have a diameter of between 1 μm and 100 μm, in particular between 2 μm and 10 μm.

Such a nozzle plate has proven to be a particularly simple way of generating an easily inhalable inhalation mist in particular from saline solution. During the discharge, liquid flows at a constant rate onto the nozzle plate and is forced through the nozzle openings and thereby nebulized.

The resulting inhalation mist enters the nebulization chamber inside the applicator head, which is connected to the applicator piece. By breathing in when the applicator piece is in place, it is possible for this inhalation mist to be inhaled.

The liquid in the liquid reservoir can be pressurized by propellant, by compressed air or by a pretensioned spring mechanism.

Although it is also possible in principle that the liquid for generating the inhalation mist is produced by means of a manual pump mechanism, it is advantageous that the inhalation device already has an energy storage means of a mechanical or chemical nature that leads to a constant liquid pressure and thus to a constant nebulization result. Besides the possibility of storing propellant in the liquid reservoir, it is also considered advantageous to have a separate reservoir of air at an overpressure, the pressure of said air acting on the liquid reservoir. A spring which is pretensioned during the production of the inhalation device or of the liquid reservoir, and which permanently applies pressure to the liquid via a piston, is also an advantageous and in particular also environmentally friendly possibility of storing energy.

The liquid reservoir itself can have a defined volume, such that air flows in for compensation purposes after the discharge. However, unventilated systems are also possible which permit a modifiable volume of the liquid reservoir via a trailing piston or a bag.

The inhalation device can have a switchable rotary outlet valve, by which the discharge channel can be opened and closed. The rotary outlet valve can be switchable by a rotation movement of the housing, or of a switch element provided on the housing or on the applicator head, with respect to the applicator piece. The valve is arranged upstream of the nozzle plate.

The housing can be configured at least in part as a rotationally symmetrical body, of which the center axis defines a main axis of extent of the housing. The housing or the switch element can be rotatable with respect to the applicator piece about this main axis of extent.

The applicator piece is preferably arranged eccentrically with respect to the rotation axis of the outlet valve, such that a moment for opening or closing the rotary valve can be introduced at the applicator piece.

The provision of a switchable outlet valve makes it possible to control the discharge of inhalation mist. Said rotary outlet valve is a valve which can be opened and closed by said possibilities of a relative rotation movement, wherein a rotary outlet valve can also be understood as a purely axially acting valve if the latter is provided with a valve mechanism by which a relative rotation movement is converted into an axial movement.

The rotation movement for the purpose of opening and closing the outlet valve has proven very simple and in particular can be carried out with one hand. When the applicator piece is fixed in the mouth region or in the mouth and nose region of the user or is also pressed simply as a mask onto the face of the user, the housing can be easily rotated with one hand for the purpose of opening or closing. A switching ring or the like can also be easily operated with the hand that is gripping the housing.

This advantageous manipulation is favored by the lateral arrangement of the applicator piece in relation to said rotation axis. This eccentric arrangement of the applicator piece allows a moment to be introduced here in order to support the required rotation movement.

The inhalation device can also have a switchable pivoting outlet valve, by which the discharge channel can be opened and closed. The pivoting outlet valve can be switchable by a pivoting movement of the applicator piece with respect to the housing.

The housing can be configured at least in part as a rotationally symmetrical body, with the center axis defining a main axis of extent of the housing. The applicator piece can be pivotable with respect to the housing about a pivot axis that is orthogonal to this main axis of extent.

A pivoting outlet valve can also be understood as a valve which is switchable by a pivoting movement between the applicator piece and housing. Such a valve can also be a valve whose valve body and valve seat are only moved axially in relation to each other, provided that a valve mechanism is provided which converts the pivoting movement into an axial movement.

The pivoting movement, in particular about a pivot axis orthogonal to the main axis of extent of the housing, has also proven to be a very advantageous way of controlling the inhalation device. Whereas a purely axial movement, in particular with the applicator piece in place, is often difficult to perform and in particular difficult to gage, the pivoting movement of the housing, which is gripped anyway during the inhalation procedure, is easy to perform and to gage.

To obtain the pivoting movement or other relative movements provided for opening the valve, an actuation handle can be provided that is movable with respect to the housing.

The inhalation device has a housing configured at least in part as a rotationally symmetrical body, with the center axis defining a main axis of extent of the housing, and the rotationally symmetrical body encloses a liquid reservoir in which the liquid is stored in pressurized form before being discharged when acted upon by propellant gas, by compressed air or by a pretensioned spring mechanism.

The inhalation device has an applicator head with a nebulization chamber and an applicator piece which is connected to the nebulization chamber and is provided laterally on the applicator head, wherein the applicator piece is designed either as a mouthpiece, to be received in the mouth of a patient, or as an inhalation mask, to sealingly cover the mouth, the nose, or the mouth and the nose, or as an adapter piece for fitting a mouthpiece or an inhalation mask.

The inhalation device has a discharge channel which connects the liquid reservoir to the applicator head, and it has a switchable rotary outlet valve, by which the discharge channel can be opened and closed.

The rotary outlet valve is switchable by a rotation movement of the housing, or of a switch element provided on the housing or on the applicator head, about the main axis of extent with respect to the applicator piece.

In such a configuration, which can also have the above-described nozzle plate but does not need to, particularly good manipulation is afforded by the fact that the applicator piece is provided laterally on the applicator head and thus eccentrically with respect to the center axis. By pressing it onto the face, the user can thus fix the applicator piece in position, such that a subsequent rotation movement of the switching element, or especially of the housing, for the purpose of opening or closing the rotary outlet valve is simple and intuitive.

For this purpose, a discharge direction defined by the applicator piece is preferably angled relative to the main axis of extent of the housing, wherein the discharge direction and the main axis of extent particularly preferably enclose an angle of between 10° and 170°, particularly preferably an angle of between 60° and 120°. In particular, a right angle (90°) can be chosen here.

An air inlet is preferably provided which opens into the nebulization chamber. By sucking in air at the applicator piece, a user can suck air into the nebulization chamber, where it is provided with atomized liquid and is then dispensed through the preferably opposite applicator piece.

The outlet valve can be assigned a spring mechanism, which is designed such that its spring force always seeks to close the outlet valve.

Such a spring mechanism can be directly part of the outlet valve. However, the spring mechanism can also be provided between the housing and the applicator head or between the housing and the applicator piece and can act only indirectly on the valve.

The applicator head can have a base part, which is connected in a rotationally fixed manner to the housing, and an outlet part, which is rotatable relative to the base part and which comprises the nebulization chamber. The applicator head and the outlet part can be guided on each other in such a way that a rotation movement of the outlet part relative to the base part causes an axial displacement of the outlet part relative to the base part, by means of which axial displacement an outlet valve of the inhalation device is switchable.

This permits a particularly simple design of the applicator head with only two relatively movable parts and overall, including the nozzle plate, only three components. The base is mounted on the housing of the inhalation device. It preferably has a guide slope, in particular as part of an internal thread or a slotted guide. The second part, the outlet part, is mounted rotatably on the base and is guided by guide portions on the guide slope, such that the rotation movement also causes an axial displacement. This axial displacement can open a valve which can be provided in the housing in the vicinity of the liquid reservoir or at the applicator head. The outlet part preferably comprises both the nebulization chamber and also an outlet opening therein with nozzle plate. The outlet part can therefore be easily cleaned as a whole under a tap.

The liquid reservoir can in particular contain an aqueous solution, mainly a saline aqueous solution. Moreover, the solution can be a buffered solution or a Ringer's solution. The aqueous solution can be provided with various additives. It can in particular contain carbohydrates, essential oils, menthol and plant extracts. It can also contain vitamins and trace elements, and also manganese or zinc. It can also contain vehicles or excipients as carriers of active substances. The liquid in the liquid reservoir can in particular also contain additives from the group comprising cinnamon oil, tea tree oil, sage oil, thyme oil and lemon balm oil.

The discharge channel can be provided at least in part with a material having an antibacterial action, in particular with silver or a silver-containing material.

The use of an antibacterial material in the discharge channel upstream from the nozzle plate has proven to be particularly advantageous, since the nozzle plate permits drying of the discharge channel only to a slight extent after discharge. The evaporation through the thin nozzle openings is low. The antibacterial material can be applied to the wall along the channel. It is also conceivable that a porous or sponge-like structure of antibacterial material is arranged in the discharge channel. It is particularly preferable if an inner side of the nozzle plate is provided with an antibacterial means, for example in the form of a silver coating.

The applicator piece and the nozzle plate can be part of a common structural unit, which is detachable from the housing without the use of tools.

The combination of the applicator piece and of the nozzle plate in a common structural unit, which is easily detachable from the housing and reattachable thereto by means of latching connections for example, affords the advantage of separate washability including the nozzle plate. This also allows this structural module to be easily exchanged for reasons of hygiene.

The problem is also solved by an inhalation device set according to the invention.

This set comprises an inhalation device of the type described above. It comprises at least two structural units that each comprise an applicator piece and a nozzle plate.

Such a set allows the inhalation device to be used by several persons without any need for concerns relating to hygiene, since each person only uses a dedicated exchangeable structural unit. Since this entails the greatest risk of contamination, the danger of infection is thus effectively avoided.

The nozzle plate of an inhalation device according to the invention comprises a large number of nozzle openings. The nozzle plate is preferably formed at least in part from silver or from a silver-containing material.

It has been found that the use of silver on a nozzle plate effectively prevents contamination, in particular also contamination in the nozzle openings.

The nozzle plate can comprise nozzle openings with a diameter of between 1 µm and 100 µm, in particular between 2 µm and 10 µm. The nozzle plate can comprise at least 9 nozzle openings, preferably at least 16 nozzle openings and particularly preferably at least 25 nozzle openings.

The entire nozzle plate can be produced from silver or a silver alloy. For economic reasons, however, this is not considered ideal.

The nozzle plate can instead have a main plate made of a material that does not contain silver or silver-containing material. A layer of silver or of silver-containing material, such as a silver alloy, can be provided on the main plate.

The layer of silver or of a silver-containing material can be applied to the main plate by vapor deposition or by immersion after the nozzle openings have been formed, such that the nozzle openings are at least partially covered with this layer on their insides.

The main plate can be produced, for example, from silicon, which has proven a particularly suitable material for this purpose. The silver or the silver-containing material is applied thereto in the form of a thin layer. This layer can be applied to the inside and/or the outside and/or in the nozzle openings themselves.

The nozzle openings can be formed after vapor deposition or immersion of the main plate for the purpose of producing the layer of silver or silver oxide, such that the nozzle openings are at least partially free of this layer on their inside.

A manufacturing approach of this kind can have important advantages in terms of economy, since large sheet-shaped blanks can be vapor-deposited, from which individual nozzle plates are produced only later. With a sufficiently large nozzle diameter, the danger of microbe colonization inside the nozzles is low, at least when the planar regions of the nozzle plate are provided internally and/or externally with a corresponding layer.

BRIEF DESCRIPTION OF THE DRAWINGS

Further advantages and aspects of the invention will become clear from the claims and from the following description of preferred illustrative embodiments of the invention, which are explained below with reference to the highly schematic drawings.

FIGS. 4a and 4b and FIGS. 5a and 5b show an inhalation device with a rotary outlet valve.

DETAILED DESCRIPTION OF THE ILLUSTRATIVE EMBODIMENTS

Figure 1A:
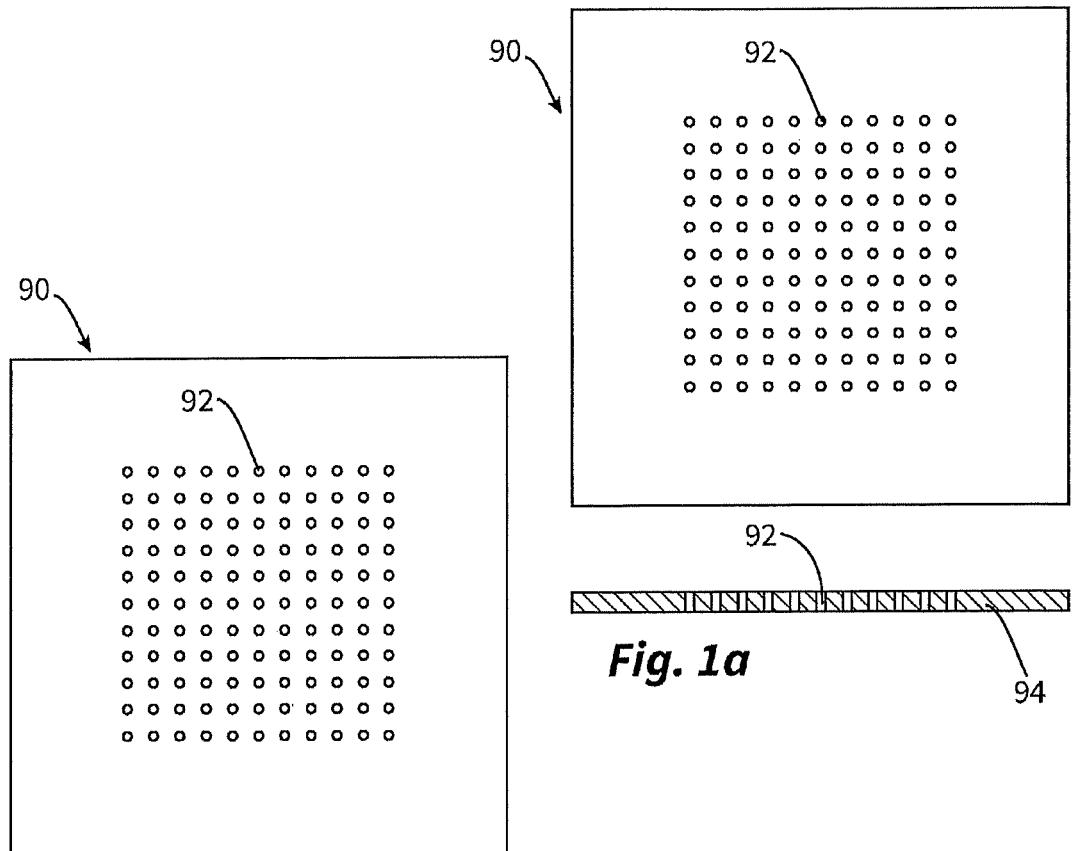
FIGS. 1a to 1c show various embodiments of nozzle plates for inhalation devices according to the invention.
Figure 1B:
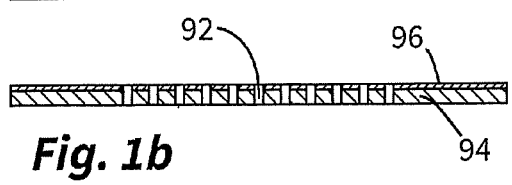
Figure 1C:
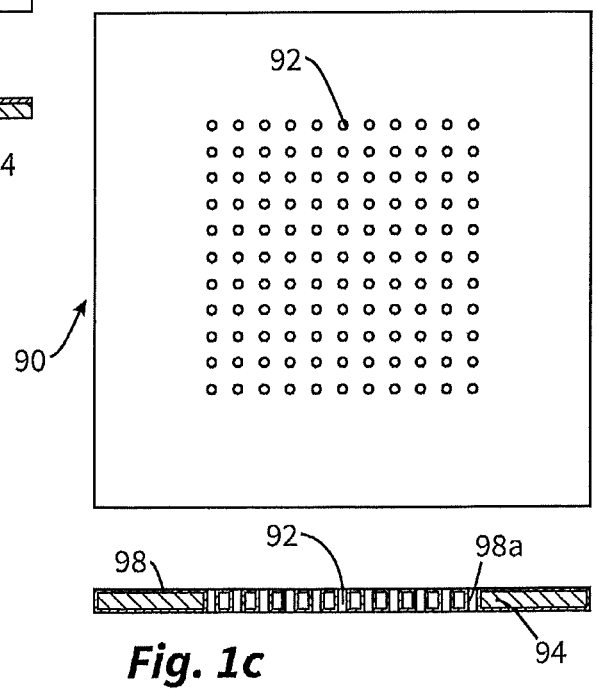

FIGS. 1a to 1c show three nozzle plates 90, each with 121 nozzle openings 92. The nozzle openings have a diameter of about 25 μm. The nozzle plates 90 shown are for use in an inhalation device according to the invention. This is described in more detail below.

The nozzle plate 90 of FIG. 1a is a particularly simple nozzle plate made uniformly of silicon. The nozzle openings 92 are introduced in a matrix pattern into this silicon. Alternatively, for the purpose of an antibacterial action, the nozzle plate 90 of FIG. 1a could also be produced entirely from silver or, for example, a silver alloy or another antibacterial material.

FIG. 1b shows a configuration in which the nozzle plate 90 has a main plate 94 and a coating 96. While the main plate 94, for example, can again be produced from silicon, the coating 96 is made of silver or a silver alloy. In this way, bacterial growth is effectively prevented. Whereas in FIG. 1b this coating 96 is shown only on one side, a plate can also be provided that is coated on two sides. A special feature of the configuration according to FIG. 1b is that the nozzle openings 92 were introduced after the coating, such that the nozzle openings 92 are not covered, or are only partially covered, on the inside by the coating. This can be advantageous for reasons of simpler production.

The configuration of FIG. 1c differs in this respect. Here too, a main plate 94 is provided which is covered by a coating 98. However, since this coating 98 was applied after the production of the nozzle openings 92, it has portions 98a that cover the inner side of the nozzle openings 92.

The partial or complete coating of silver or of a silver alloy has an antibacterial action. If the nozzle plate 90 is coated on the downstream side, it acts in particular against bacterial growth that can occur in the deposited liquid film on this side. A corresponding coating on the upstream side acts in particular on the liquid that still lies in front of the nozzle openings 92 toward the end of a discharging operation. An antibacterial action is particularly useful there since evaporation of the liquid through the nozzle openings 92 takes place only very slowly there, and the risk of bacterial growth there is therefore correspondingly high.

Figures 2, 3A, 3B:
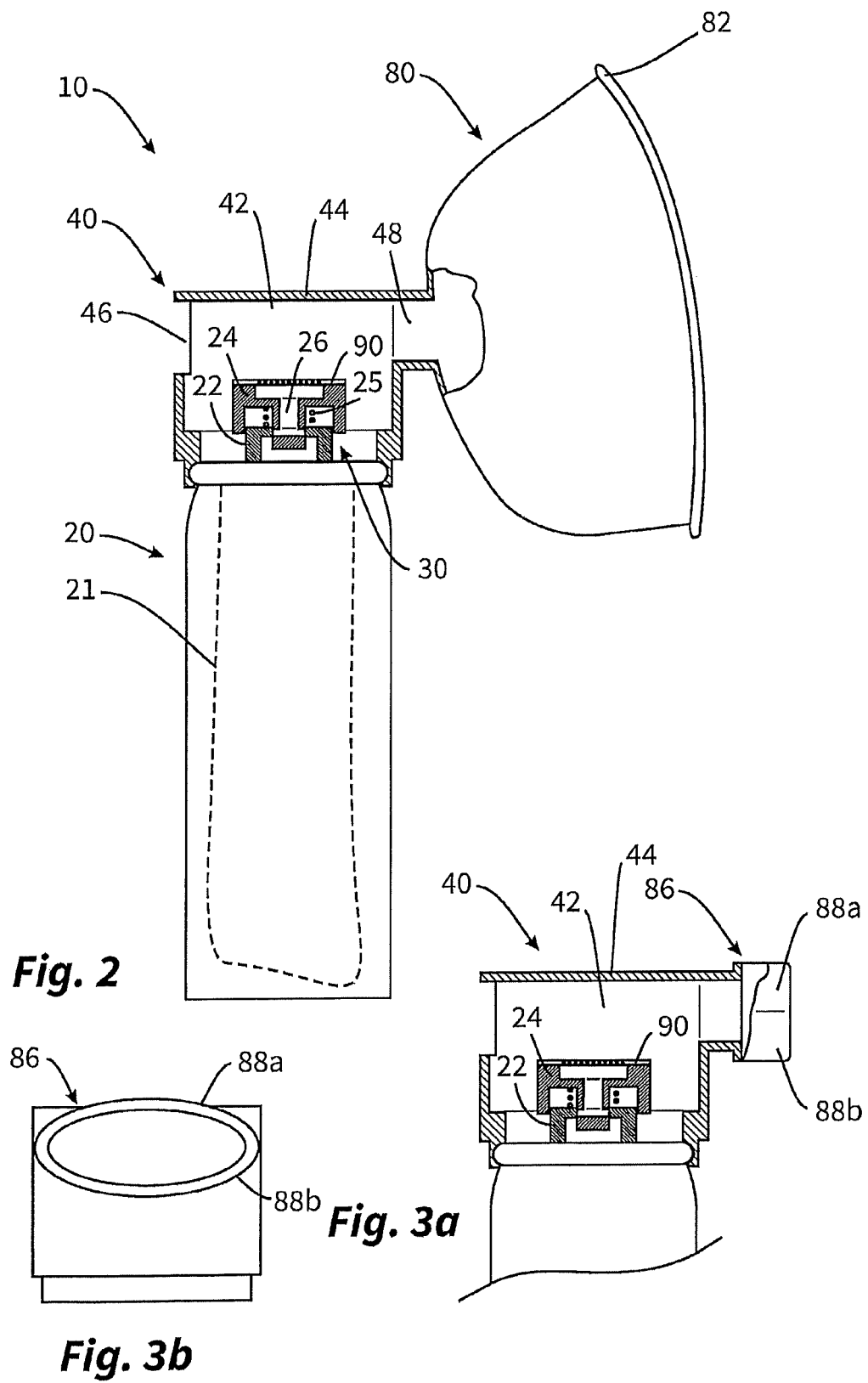
FIG. 2 and FIGS. 3a and 3b show particularly simple embodiments of inhalation devices.
Figure 6A:
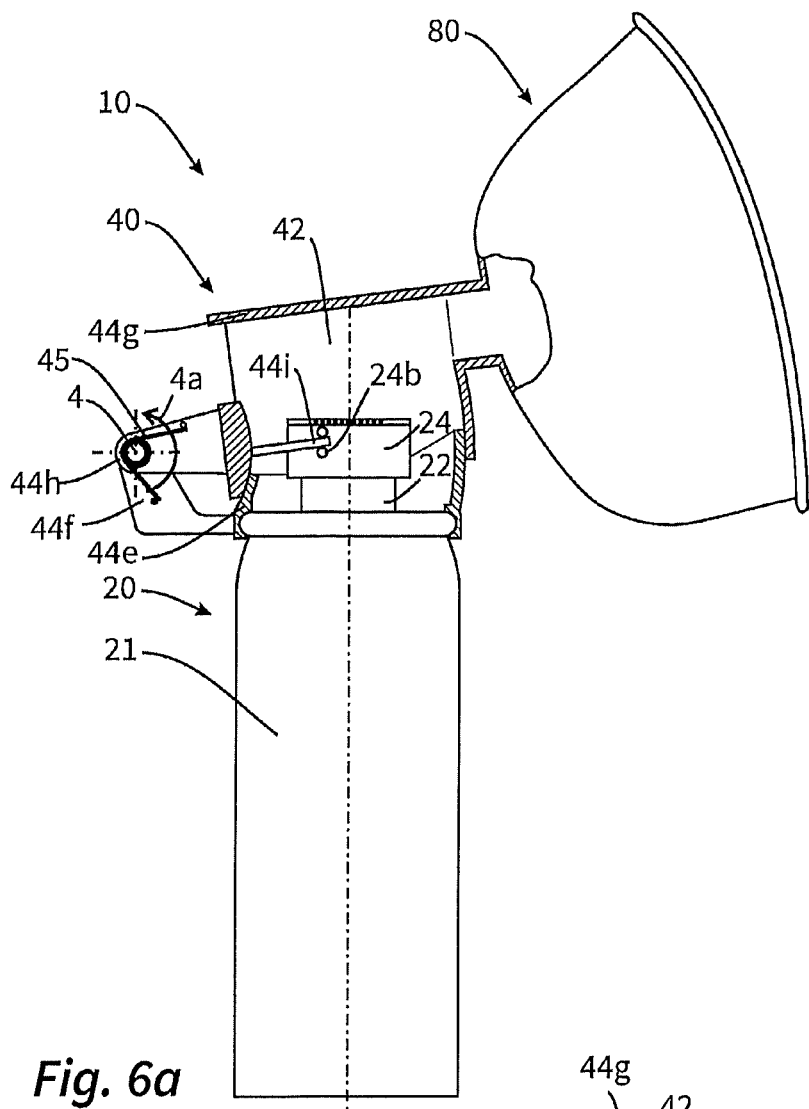
FIGS. 6a, 6b and 6c show an inhalation device with a pivoting outlet valve.
Figure 6B:
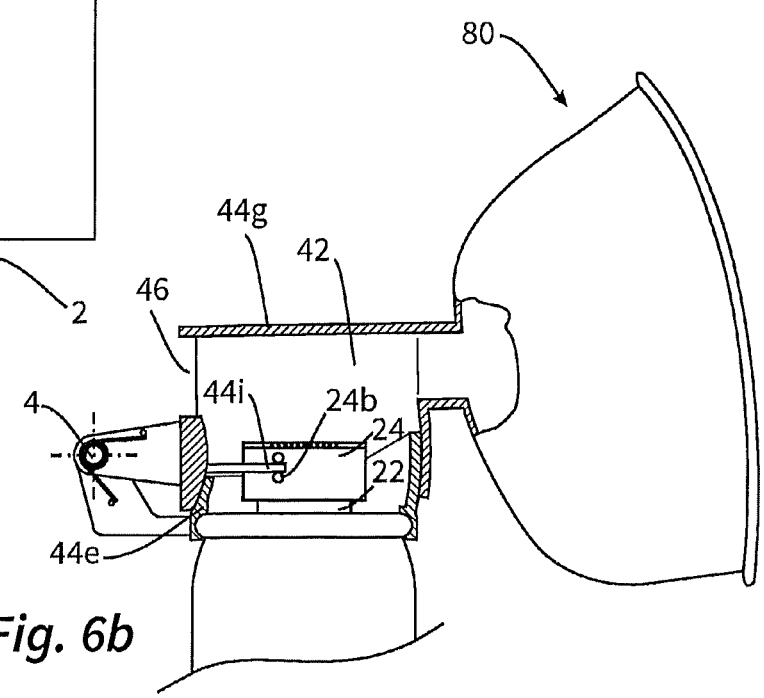
Figure 6C:
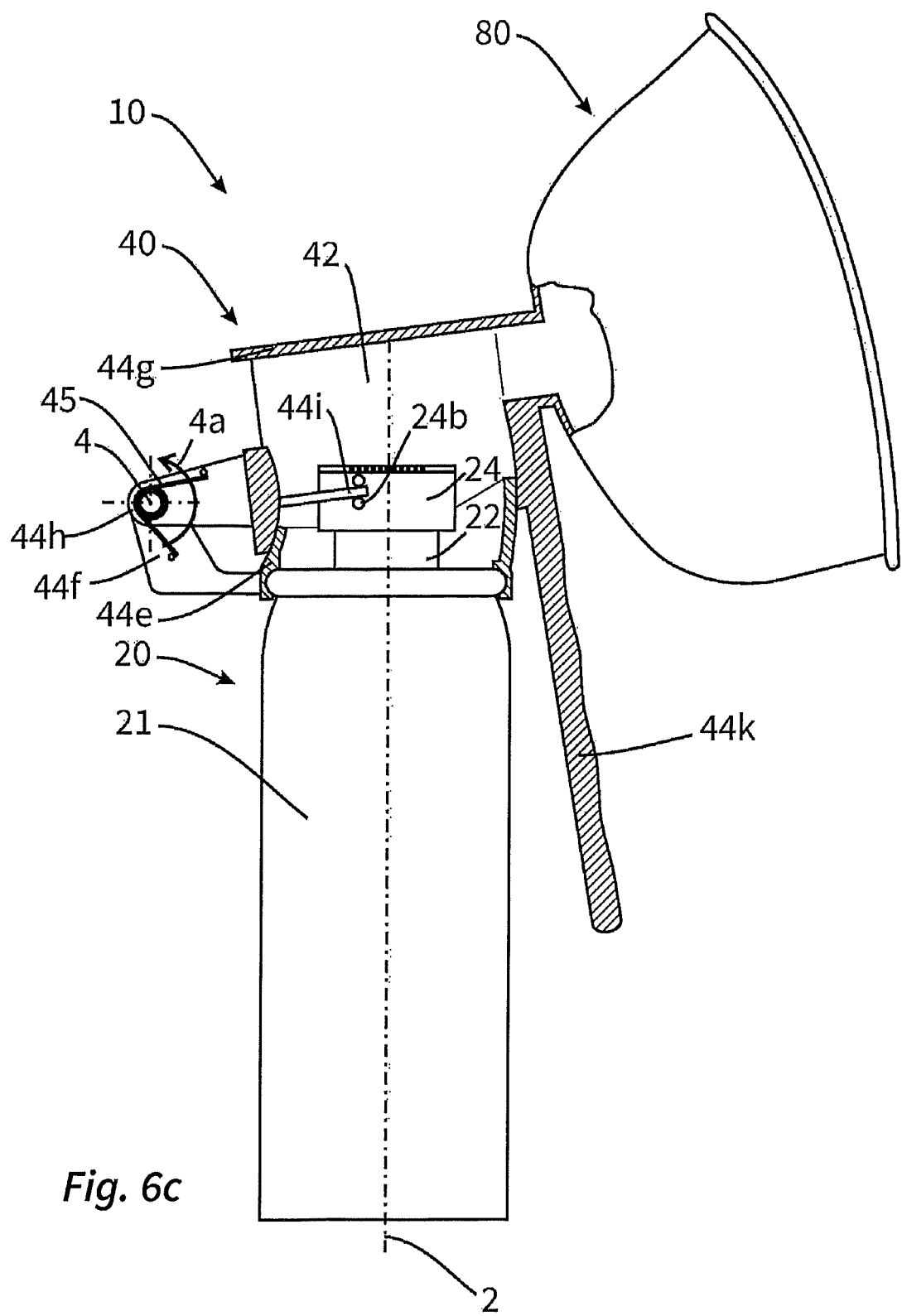
Figure 7A:
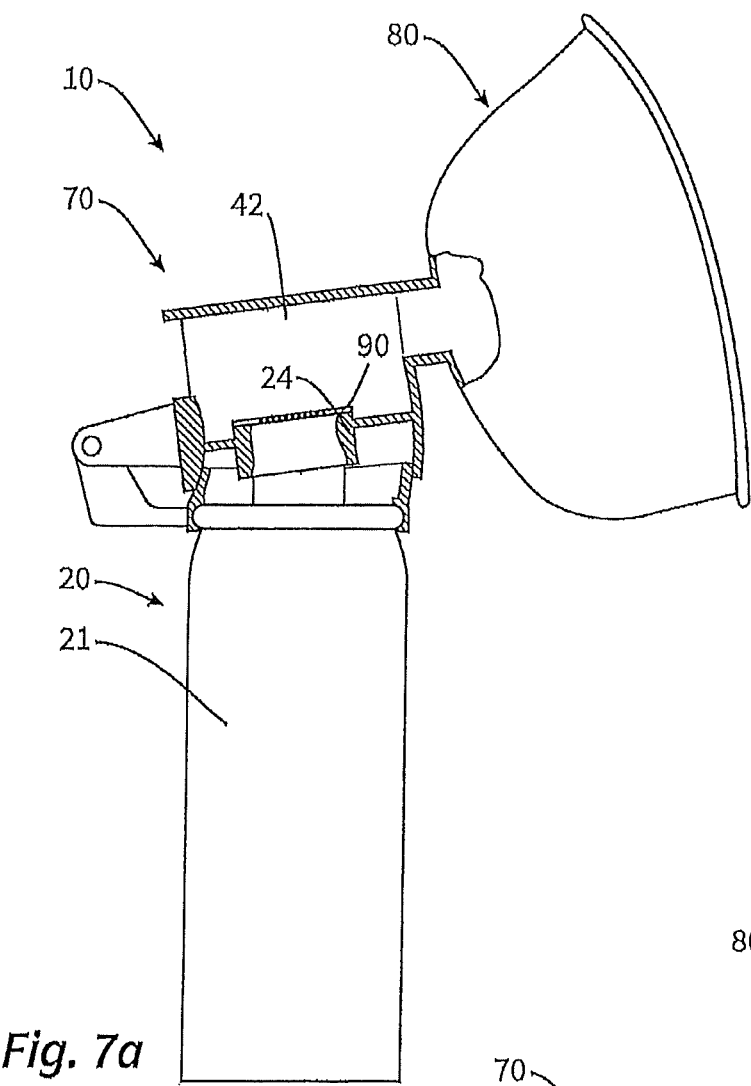
FIGS. 7a and 7b together show an inhalation device set.
Figure 7B:
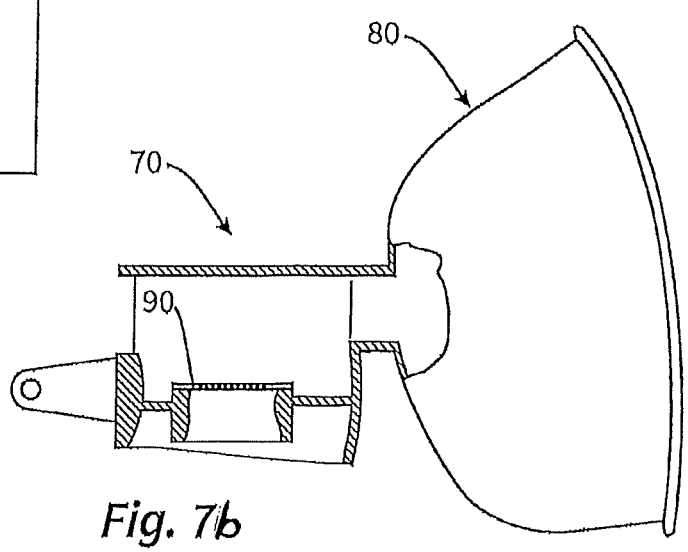
Figures 8A, 8B:
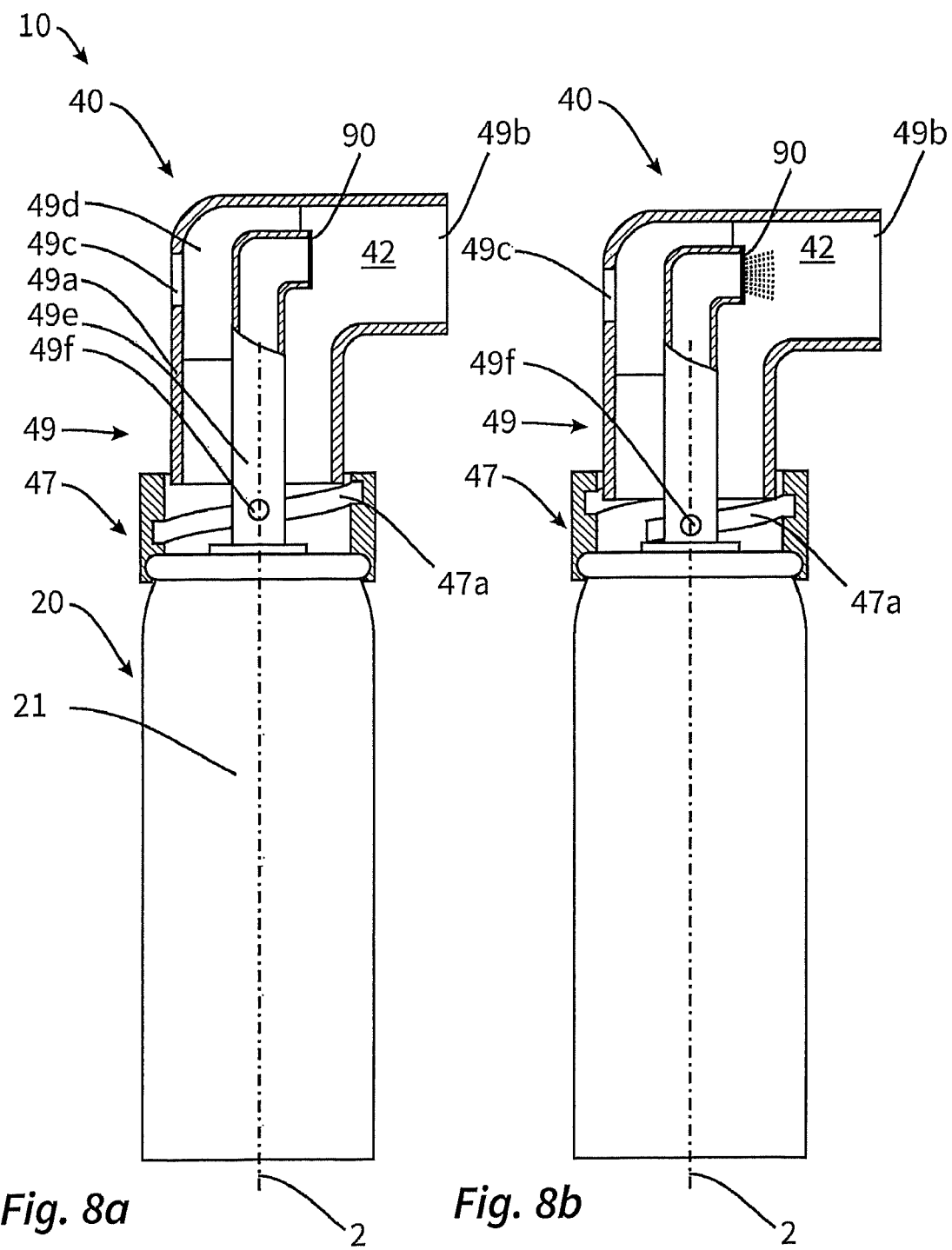
FIGS. 8a and 8b show a further inhalation device 10, which is characterized by a very simple structure.
Figure 9A:
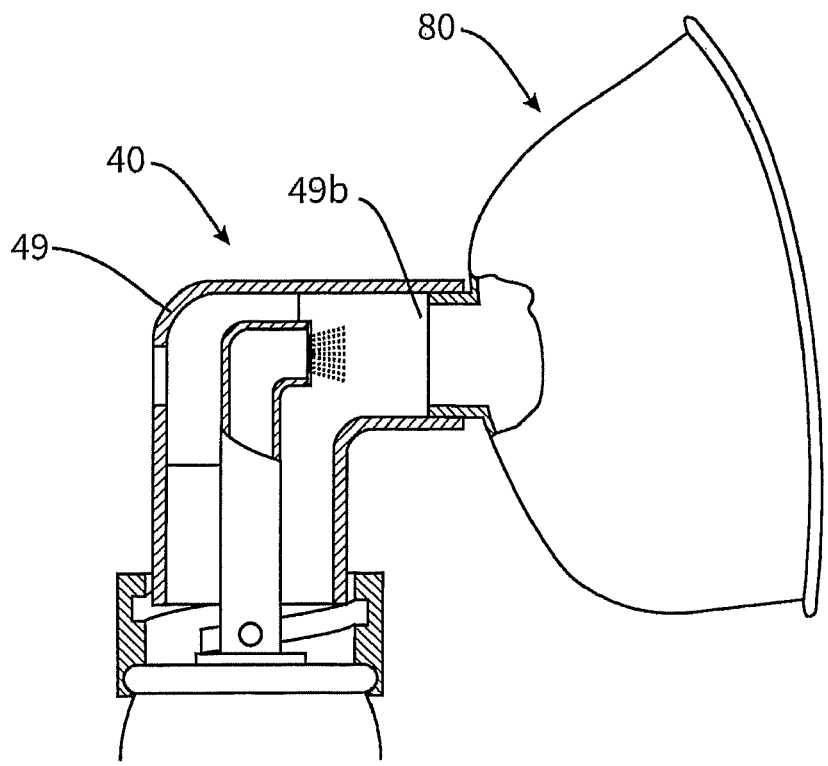
FIGS. 9a and 9b show an addition to the inhalation device of FIGS. 8a and 8b in the form of an attachable mouthpiece and an attachable inhalation device.
Figure 9B:
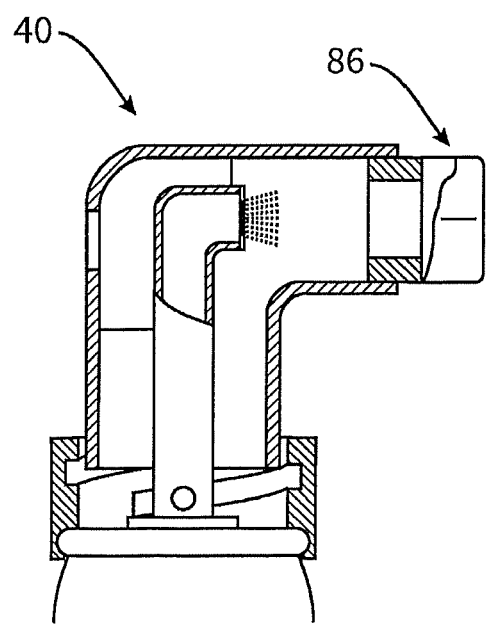

FIG. 2 and FIGS. 3a and 3b show very simple inhalation devices 10 using such nozzle plates 90. The inhalation devices shown in the other figures are based on the functionality of these simple inhalation devices. The inhalation device 10 of FIG. 2 has a cylindrical housing 20 which is designed as a pressurized container and in which a saline solution is stored.

Alternatively, it could also store an aqueous solution in the form of a Ringer's solution or a buffered solution, an aqueous solution with at least one of the additives carbohydrates, essential oils, menthol and plant extracts, an aqueous solution containing vitamins, trace elements, manganese or zinc, or an aqueous solution with at least one of the additives from the group comprising cinnamon oil, tea tree oil, sage oil, thyme oil, lemon balm oil.

The saline solution can be pressurized by means of propellant. An alternative to this is that the pressurized container is filled with air at an overpressure and has a bag-shaped liquid reservoir 21, which is shown for example by dotted lines in FIG. 2. The overpressure seeks to convey the liquid from the liquid reservoir 21 in the direction of a discharge channel 26 and thus to the nozzle plate 90. Between the nozzle plate 90 and the liquid reservoir 21, a valve 30 is provided which is formed jointly by a neck 22, which is fixed in position on the housing 20, and by a slide 24 which is movable by contrast in the vertical direction. As will be seen from the view in FIG. 2, the slide has to be pressed down counter to the force of a spring (not shown) so that the discharge channel 26 is opened. As soon as this is the case, liquid can flow through the discharge channel 26 to the nozzle plate 90. Under the substantially constant pressure that is then present there, this liquid is forced through the nozzle openings 92 of the nozzle plate 90 and thus generates an inhalation mist.

An applicator head 40 is fitted onto the housing 20. This applicator head 40 surrounds a nebulization chamber 42, into which the liquid that has passed through the nozzle plate 90 enters in nebulized form. The housing 44 of the applicator head 40 has an air inlet 46. Lying opposite the latter, an air outlet 48 is provided, to which an applicator piece is attached. The applicator piece in FIG. 2 is an inhalation mask 80. The latter is intended to be placed on the face of the user such that it completely covers the mouth and nose. Each breathing process therefore has the effect that air is drawn through the applicator head 40, where it is prepared for inhalation by means of the described nebulization.

As in the following illustrative embodiments too, the nozzle plate 90 can be configured as shown in FIGS. 1a to 1c. An outwardly facing antibacterial layer can prevent bacterial growth of the kind that can form on the nozzle plate 90 in the deposition of the inhalation mist. A coating facing toward the channel 26 ensures that no bacterial growth is possible in the quantity of liquid lying on the nozzle plate 90 on the inside. This is particularly helpful since the liquid located on the other side of the valve 30 can evaporate only with difficulty through the nozzle openings, such that the risk of contamination is comparatively high here.

FIGS. 3a and 3b show the second possibility, besides the inhalation mask, of an an applicator piece for use according to the invention. This is a mouthpiece 86 which has an elongate shape corresponding to the shape of the human mouth. The mouthpiece 86 is provided at the top and bottom with bearing surfaces 88a, 88b on which the lips are placed and which, in the context of some of the valve devices described below, are expedient for introducing a supporting moment here.

In the embodiments of FIG. 2 and FIGS. 3a and 3b, the way in which the valve is actuated is not shown in detail. The slide could be pressed down, for example, by having an actuation lever (not shown) which is guided through a slit in the wall of the housing 44.

Particular embodiments of the valve 30 or of the associated opening mechanism will be seen from the following illustrations.

In the embodiment according to FIGS. 4a and 4b, the housing of the applicator head 40 is configured in two parts.

It has a lower portion 44a, which is mounted secure against rotation on the housing 20. By contrast, an upper portion 44b is rotatable about the axis 2. From this upper portion 44b, two webs 44c extend as far as the slide 24 and into oblique guide grooves 24a provided on the slide 24. Since the slide 24 is rotationally fixed with respect to the housing in a manner not shown in detail, a rotation of the upper housing portion 44b together with the applicator piece 80 in relation to the housing 20 has the effect that the slide 24 is displaced axially with respect to the housing 20, thereby permitting activation and deactivation of the generation of inhalation mist by opening and closing of the valve 30. It is particularly advantageous that this switching operation can be carried out with one hand. During use of the inhalation device 10, the housing 20 is usually grasped with one hand and the inhalation mask 80 thus also pressed against the face. In this position, the housing 20 can be easily rotated as a whole and together with the slide 24 in order to initiate the generation of the inhalation mist.

This one-handed operation is favored by the fact that the applicator piece is arranged eccentrically with respect to the axis 2, such that it allows a supporting moment to be introduced during a rotation movement or pivoting movement of the housing 20 with respect to the applicator piece. In the case of the inhalation mask 80, this is achieved by a circumferential sealing edge 82, which rests on the face and can be supported there. In the case of the mouthpiece 86, this is achieved by the bearing surfaces 88*a*, 88*b* which are provided for the lips to bear on. By gently pressing the lips together, the mouthpiece is fixed such that a relative movement of the housing 20 is easily possible for the purpose of switching a valve.

FIG. 4*a* shows the inhalation device 10 with the discharge valve 30 closed. FIG. 4*b* shows the open state.

The configuration in FIGS. 5*a* and 5*b* is a variation of the configuration in FIGS. 4*a* and 4*b*. The housing 44 of the applicator head 40 is here again provided in one piece. However, a separate switch element 50 is mounted on the applicator head 40, which is likewise rotatable about the rotation axis. The switch element 50 has a switching ring 51*a*, accessible from the outside, and a web 51*b* projecting inwardly into the slotted guide tracks of the slide 24. By turning the switch element 50 via the switching ring 51*a*, the valve 30 can be opened and closed.

In the configuration according to FIGS. 6*a* and 6*b*, the housing 44 of the discharge head 40 is again in two parts. A lower housing portion 44*e* is mounted fixedly on the housing 20. By contrast, an upper housing portion 44*g*, on which the inhalation mask 80 is also provided, is pivotable about a pivot axis 4. For this purpose, both the lower housing portion 44*e* and the upper housing portion 44*g* have webs 44*f*, 44*h* which are articulated pivotably on each other and which are mounted on each other in an articulated manner. A leg spring 45 is provided between these webs and applies a torque to the upper housing portion 44*g* with respect to the lower housing portion 44*e* in the direction of the arrow 4*a*.

For the actuation of the valve 30, a web 44*i* is provided on the upper housing portion 44*g* and interacts with a cam 24*b* on the slide 24. If an only slight pivoting movement takes place by a few degrees relative to the initial position in FIG. 6*a*, the web 44*b* pushes the slide 24 downward relative to the housing 20 by application of force of the cam 24*b*, thus causing the valve 30 to open.

As in the embodiments of FIGS. 4*a* and 4*b*, a very simple one-handed operation is also possible here. When the inhalation mask 80 is pressed against the face, the pivoting movement of the housing 20 and thus the opening and closing of the valve 30 can be effected with one hand.

FIG. 6*c* shows an expanded configuration in which, in addition to the components of the embodiment in FIGS. 6*a* and 6*b*, an actuation lever 44*k* is provided on the housing of the applicator head 40. By grasping the housing 20 and the actuation lever 44*k* with one hand and tightening the grip, the valve can be caused to pivot and thus open.

FIG. 7*a* shows an inhalation device 10 similar to that of FIGS. 6*a* and 6*b*. The special feature here is that the slide 24 is integrated in the upper housing portion. The valve should be so designed that it closes when the slide 24 is detached.

This results in a coherent structural unit 70, which is shown separately in FIG. 7*b*, and which permits simple cleaning.

An inhalation device set according to the invention comprises a plurality of these structural units 70, so that the latter can be exchanged for reasons of hygiene.

FIGS. 8*a* and 8*b* show a further inhalation device 10. Here, an applicator head 40 is constructed from very few components and is therefore inexpensive to produce.

The applicator head has a base 47 which is connected to the housing 20 in a rotationally fixed manner. The base has the shape of a ring, and two guide tracks 47*a* shaped as portions of a helix are provided lying opposite each other on the inner side.

An outlet part 49 is inserted into the base 47. This outlet part 49 has a curved outer tube 49*a*, which ends in an opening 49*b* that can be used as a mouthpiece. The outer tube 49*a* has an inflow opening 49*c* on the side lying opposite the opening 49*b*.

An inner tube 49*e*, which is fixed in position in the outer tube 49*a* and preferably integrally connected to the outer tube 49*a*, is in this case connected to the outer tube 49*a* via a rib 49*d*. The inner tube terminates in a nozzle plate 90. Liquid, which is conveyed through the inner tube to the nozzle plate 90, is discharged there into the nebulization chamber 42. The user can inhale the nebulized liquid by providing suction at the opening 49*b*.

To control the nebulization, the outlet part 49 is rotatable with respect to the base 47 about the axis 2. Guide pins 49*f* are provided on the outlet part and in the present case extend outward from an outer side of the inner tube 49*e* into the guide tracks 47*a*. A rotation movement of the outlet part 49 relative to the base 47 therefore also causes an axial relative movement in the direction of the axis 2. This causes the opening and closing of a valve, which is provided inside the housing 20 in a manner not shown.

The end of the outer tube 49 with the opening 49*b* can be used directly as a mouthpiece. FIGS. 9*a* and 9*b*, however, illustrate a further possibility. Thus, an inhalation device with an applicator head according to FIGS. 8*a* and 8*b* can also be accompanied by a separate mouthpiece 86 or an inhalation mask 80. These each comprise a plug portion which can be pushed into the opening 49*b* and is held there by form-fit or force-fit engagement. Thus, the inhalation device can be adapted to individual requirements.

The invention claimed is:

1. An inhalation device for inhaling a liquid in nebulized form, comprising:

a housing configured in part as a rotationally symmetrical body with a center axis defining a main axis of extent of the housing, the rotationally symmetrical body enclosing a liquid reservoir in which a liquid is stored in pressurized form by application of a propellant gas or compressed air, or by a pretensioned spring mechanism, before being discharged;

an applicator head comprising:
  a nebulization chamber; and
  an applicator piece connected to the nebulization chamber, the applicator piece being configured as a mouthpiece to be received in a mouth of a patient, as an inhalation mask to sealingly cover a mouth, a nose or a mouth and nose of a patient, or as an adapter piece for fitting a mouthpiece or an inhalation mask;

a discharge channel connecting the liquid reservoir to the nebulization chamber of the applicator head; and an outlet valve disposed to open and close the discharge channel, wherein a rotational movement of the housing about the main axis of extent with respect to the applicator piece switches the outlet valve to open the discharge channel and discharge the liquid from the inhalation device while the outlet valve is open, the applicator piece being oriented laterally relative to the main axis of extent of the housing such that the applicator piece allows the patient to generate a force adjacent a mouth area which permits the rotational movement of the housing with respect to the applicator piece.

2. The inhalation device according to claim 1, further including an air inlet opening into the nebulization chamber, the air inlet and the applicator piece being disposed on opposite sides of the nebulization chamber.

3. The inhalation device according to claim 1, further including a nozzle plate disposed at a downstream end of the discharge channel, the nozzle plate including a plurality of nozzle openings which generate an inhalation mist, the nozzle openings being disposed to convey the liquid from the liquid reservoir into the nebulization chamber.

4. The inhalation device according to claim 3, further including a structural unit, the applicator piece and the nozzle plate forming part of the structural unit, the structural unit being configured for detachment from the housing without the use of a tool.

5. The inhalation device according to claim 3, wherein the nozzle plate includes one of the following:

the nozzle plate is formed in part from silver or from a silver-containing material; or the nozzle openings have a diameter of between 1 μm and 100 μm; or the nozzle plate comprises at least nine of the nozzle openings.

6. The inhalation device according to claim 3, wherein the nozzle plate comprises a main plate constructed of a material that does not contain silver or silver-containing material, and a layer of silver or of silver-containing material is provided on the main plate.

7. An inhalation device set comprising an inhalation device according to claim 3, the inhalation device set comprising at least two structural units, each structural unit comprising an applicator piece and a nozzle plate.

8. The inhalation device according to claim 1, wherein the applicator piece defines a discharge direction oriented at an angle relative to the main axis of extent, and the angle of the discharge direction is between 10° and 170°.

9. The inhalation device according to claim 1, further including a spring mechanism configured to bias the outlet valve towards a closed position thereof in which the discharge channel is closed.

10. The inhalation device according to claim 1, wherein the applicator head has a base part connected in a rotationally fixed manner to the housing, and an outlet part rotatable relative to the base part and comprising the nebulization chamber, the base part and the outlet part being guided on one another such that a rotational movement of the outlet part relative to the base part axially displaces the outlet part relative to the base part and axially displaces the outlet valve and switches same to an open position to open the discharge channel.

11. The inhalation device according to claim 1, further including one of the following:

the discharge channel is provided in part with a material having an antibacterial action; or the applicator piece is configured as a mouthpiece having an outlet with a width greater than a height, the mouthpiece having a top face with a bearing surface configured for bearing on an upper lip and a bottom face with a bearing surface configured for bearing on a lower lip; or the applicator piece is configured as an inhalation mask with a circumferential sealing edge configured for bearing on a face of a patient, the sealing edge being dimensioned to enclose the mouth, the nose, or the mouth and the nose; or the applicator piece is configured as an adapter piece for fitting a mouthpiece or an inhalation mask.

12. The inhalation device according to claim 1, wherein the outlet valve includes a valve part mounted for movement relative to the housing, the applicator head having a housing portion non-movably connected to the applicator piece and cooperatively engaged with the valve part, and the housing portion and the valve part are configured to transform the rotational movement of the housing into an axial displacement of the outlet valve to switch same and open the discharge channel.

13. The inhalation device according to claim 12, wherein the valve part is mounted for axial movement relative to the housing and is rotationally fixed relative to the housing, and the rotational movement of the housing relative to the applicator piece and the housing portion moves the valve part axially to cause the axial displacement of the outlet valve.

14. An inhalation device comprising:

a housing including a rotationally symmetrical body defining a center axis, said body including a liquid reservoir storing liquid in a pressurized state prior to discharge of same from said inhalation device;

an applicator head connected to said housing and including a nebulization chamber, said applicator head further including an application component in fluid communication with said nebulization chamber, said application component having a portion configured for directing the liquid to a user's mouth, said housing and said application component being connected to one another for relative rotation with respect to one another about the central axis;

a discharge channel fluidly interconnecting said liquid reservoir and said nebulization chamber; and an outlet valve switchable between an open position in which said discharge channel is in fluid communication with said liquid reservoir to permit discharge of the liquid therefrom to said nebulization chamber, and a closed position in which said discharge channel is blocked from fluid communication with said liquid reservoir to prevent discharge of the liquid therefrom to said nebulization chamber, wherein rotation of said housing relative to said application component about the center axis switches said outlet valve to the open position and causes discharge of the liquid in said liquid reservoir from said inhalation device while said outlet valve is in the open position, said portion of said application component being oriented eccentrically relative to the center axis of said housing such that said portion of said application component allows the user to generate a force adjacent a mouth area which permits the rotational movement of said housing relative to said application component.

15. The inhalation device according to claim 14, wherein said outlet valve includes a valve part mounted for movement relative to said housing, said applicator head having a first portion non-rotatably mounted on said housing and a second portion, said first portion and said housing being rotatable with respect to said second portion about the center axis, said second portion being non-movably connected to said portion of said application component and operatively connected to said valve part such that rotation of said housing about the center axis relative to said second portion moves said valve part in a direction substantially parallel to the center axis and relative to said housing to switch said outlet valve to the open position.

16. The inhalation device according to claim 15, wherein one of said second portion and said valve part comprises a web and the other of said second portion and said valve part comprises a guide groove in which said web is engaged, wherein rotation of said housing relative to said application component and said second portion displaces said web within said guide groove and said guide groove is configured to convert the rotation of said housing relative to said application component and said second portion to an axial displacement of said valve part and cause an axial displacement of said outlet valve to switch said outlet valve to the open position.

17. The inhalation device according to claim 14, wherein said outlet valve includes a valve part mounted for movement relative to said housing, said applicator head having a base part connected in a rotationally fixed manner to said housing and an outlet part, —said base part and said housing being rotatable with respect to said outlet part, said outlet part defining said nebulization chamber and being non-movably connected to said application component and being operatively connected to said valve part such that rotation of said housing about the center axis relative to said outlet part axially displaces said outlet part relative to said base part and axially displaces said valve part to switch said outlet valve to the open position.

18. An inhalation device for inhaling a liquid in nebulized form, comprising:
a housing configured in part as a rotationally symmetrical body with a center axis defining a main axis of extent of the housing, the rotationally symmetrical body enclosing a liquid reservoir in which a liquid is stored in pressurized form by application of a propellant gas or compressed air, or by a pretensioned spring mechanism, before being discharged;
an applicator head comprising:
a nebulization chamber; and
an applicator piece connected to the nebulization chamber and in fluid communication therewith, the applicator piece being configured as a mouthpiece to be received in a mouth of a patient, as an inhalation mask to sealingly cover a mouth, a nose or a mouth and nose of a patient, or as an adapter piece configured for non-movably connecting to a mouthpiece or an inhalation mask;
a discharge channel connecting the liquid reservoir to the nebulization chamber of the applicator head; and
an outlet valve disposed to open and close the discharge channel, the applicator piece and the outlet valve being operatively connected to one another such that a rotational movement of the housing about the main axis of extent with respect to the applicator piece axially displaces the outlet valve and switches the outlet valve to open the discharge channel and discharge the liquid from the inhalation device while the outlet valve is open, part of the applicator piece being oriented laterally relative to the main axis of extent of the housing such that the part of the applicator piece allows a patient to generate a force adjacent a mouth area which permits the rotational movement of the housing with respect to the applicator piece.

19. The inhalation device according to claim 18, wherein the outlet valve includes a valve part mounted for movement relative to the housing, the applicator head having a housing portion non-movably connected to the applicator piece and cooperatively engaged with the valve part, and the housing portion and the valve part are configured to transform the rotational movement of the housing into an axial displacement of the outlet valve to switch same and open the discharge channel.

20. The inhalation device according to claim 19, wherein the valve part is mounted for axial movement relative to the housing and is rotationally fixed relative to the housing, and the rotational movement of the housing relative to the applicator piece and the housing portion moves the valve part axially to cause the axial displacement of the outlet valve.

21. The inhalation device according to claim 20, wherein one of the housing portion of the applicator head or the valve part includes a web, and the other of the housing portion of the applicator head or the valve part includes a guide groove in which the web is engaged, wherein the rotational movement of the housing relative to the applicator piece and the housing portion displaces the web within the groove to move the valve part axially and cause the axial displacement of the outlet valve.

22. The inhalation device according to claim 18, wherein the applicator head has a base part connected in a rotationally fixed manner to the housing and an outlet part rotatable relative to the base part and non-movably connected to the applicator piece and comprising the nebulization chamber, the base part and the outlet part being configured to transform the rotational movement of the housing into an axial displacement of the outlet valve to switch same and open the discharge channel.

23. The inhalation device according to claim 22, wherein the rotational movement of the housing relative to the applicator piece and the outlet part causes a rotational movement of the outlet part and the applicator piece relative to the base part and axially displaces the outlet part relative to the base part to cause the axial displacement of the outlet valve.

24. The inhalation device according to claim 23, wherein one of the base part or the outlet part includes a guide pin and the other of the base part or the outlet part includes a guide groove in which the guide pin is engaged, wherein the rotational movement of the housing relative to the applicator piece and the outlet part displaces the guide pin within the guide groove to move the outlet part axially and cause the axial displacement of the outlet valve.

* * * * *